United States Patent
Hanawa et al.

(10) Patent No.: US 8,552,408 B2
(45) Date of Patent: Oct. 8, 2013

(54) PARTICLE BEAM IRRADIATION APPARATUS AND CONTROL METHOD OF THE PARTICLE BEAM IRRADIATION APPARATUS

(75) Inventors: Katsushi Hanawa, Kita-Ku (JP);
Yasushi Iseki, Yokohama (JP);
Nobukazu Kakutani, Yokohama (JP);
Takuji Furukawa, Chiba (JP); Taku Inaniwa, Chiba (JP); Shinji Sato, Chiba (JP); Kouji Noda, Chiba (JP)

(73) Assignees: Kabushiki Kaisha Toshiba, Tokyo (JP);
National Institute of Radiological Sciences, Chiba-Shi (JP)

( * ) Notice: Subject to any disclaimer, the term of this patent is extended or adjusted under 35 U.S.C. 154(b) by 0 days.

(21) Appl. No.: 13/577,741

(22) PCT Filed: Feb. 7, 2011

(86) PCT No.: PCT/JP2011/052522
§ 371 (c)(1),
(2), (4) Date: Aug. 8, 2012

(87) PCT Pub. No.: WO2011/099448
PCT Pub. Date: Aug. 18, 2011

(65) Prior Publication Data
US 2012/0305790 A1    Dec. 6, 2012

(30) Foreign Application Priority Data

Feb. 10, 2010 (JP) .................................. 2010-028046

(51) Int. Cl.
*A61N 5/10* (2006.01)
(52) U.S. Cl.
USPC .................. 250/492.3; 250/491.1; 250/492.1; 250/423 R; 250/424; 250/397
(58) Field of Classification Search
USPC ............ 250/491.1, 492.1, 492.3, 423 R, 424, 250/396 R, 397, 398
See application file for complete search history.

(56) References Cited

U.S. PATENT DOCUMENTS

| 5,008,914 A * | 4/1991 | Moore ........................ 378/108 |
| 6,810,107 B2 * | 10/2004 | Steinberg ...................... 378/65 |
| 7,190,763 B2 * | 3/2007 | Mungilwar ..................... 378/97 |
| 7,723,696 B2 * | 5/2010 | Shirakawa et al. ........... 250/395 |
| 7,758,241 B2 * | 7/2010 | Sliski et al. .................. 378/203 |

(Continued)

FOREIGN PATENT DOCUMENTS

| JP | 11 233300 | 8/1999 |
| JP | 2007 296321 | 11/2007 |

(Continued)

OTHER PUBLICATIONS

International Search Report Issued Mar. 8, 2011 in PCT/JP11/52522 Filed Feb. 7, 2011.

(Continued)

*Primary Examiner* — Michael Logie
(74) *Attorney, Agent, or Firm* — Oblon, Spivak, McClelland, Maier & Neustadt, L.L.P.

(57) ABSTRACT

Provided is a particle beam irradiation apparatus capable of highly reliable measurement of a dose of each beam and capable of highly sensitive measurement of a leakage dose caused by momentary beam emission. The particle beam irradiation apparatus according to the present invention includes: an emission control portion that controls emission and termination of a particle beam; a control portion that sequentially changes an irradiation position of the particle beam relative to an affected area; first and second dosimeters that measure dose rates of the particle beam directed to the affected area; and an abnormality determination portion that accumulates the dose rates output from the first and second dosimeters for each of predetermined determination periods to calculate first and second sectional dose measurement values and that performs second abnormality determination of determining that there is an abnormality and outputs an interlock signal for terminating the emission of the particle beam in at least one of a case in which the first sectional dose measurement value exceeds a predetermined first reference range and a case in which the second sectional dose measurement value exceeds a predetermined second reference range.

12 Claims, 15 Drawing Sheets

(56) References Cited

U.S. PATENT DOCUMENTS

2006/0231775 A1* 10/2006 Harada .................. 250/492.3
2006/0273264 A1* 12/2006 Nakayama et al. ........ 250/492.3
2007/0252093 A1* 11/2007 Fujimaki et al. ......... 250/492.3
2010/0082294 A1*  4/2010 Adnani .................... 702/182

FOREIGN PATENT DOCUMENTS

| | | |
|---|---|---|
| JP | 2008 175829 | 7/2008 |
| JP | 2009 39219 | 2/2009 |
| JP | 2009 45229 | 3/2009 |
| JP | 2009 66106 | 4/2009 |
| JP | 2009 279046 | 12/2009 |

OTHER PUBLICATIONS

International Preliminary Report on Patentability Issued Sep. 18, 2012 in PCT/JP11/52522 Filed Feb. 7, 2011.

* cited by examiner

PATTERN FILE 40

| SETTING VALUE OF RANGE SHIFTER THICKNESS | SCANNING ELECTROMAGNET EXCITING CURRENT VALUE (X) | SCANNING ELECTROMAGNET EXCITING CURRENT VALUE (Y) | MAIN DOSIMETER PRESET COUNT VALUE A1 | MAIN DOSIMETER PRESET COUNT VALUE A2 | SUB DOSIMETER PRESET COUNT VALUE B1 | SUB DOSIMETER PRESET COUNT VALUE B2 |
|---|---|---|---|---|---|---|
| 10 | 5 | 5 | 300000 | 3000 | 330000 | 3100 |
| 10 | 10 | 5 | 280000 | 3000 | 308000 | 3100 |
| 10 | 15 | 10 | 250000 | 3000 | 275000 | 3100 |
| 10 | 25 | 10 | 280000 | 3000 | 308000 | 3100 |
| 12 | 5 | 5 | 50000 | 3000 | 55000 | 3100 |
| 12 | 15 | 10 | 51000 | 3000 | 56100 | 3100 |
| 12 | 20 | 10 | 52000 | 3000 | 57200 | 3100 |
| 15 | 5 | 15 | 19000 | 3000 | 20900 | 3100 |
| 15 | 15 | 15 | 20000 | 3000 | 22000 | 3100 |
| ... | ... | ... | ... | ... | ... | ... |
| 20 | 25 | 25 | 15000 | 300 | 16500 | 310 |

FIG. 5

PATTERN FILE 40a

| SETTING VALUE OF RANGE SHIFTER THICKNESS | SCANNING ELECTROMAGNET EXCITING CURRENT VALUE (X) | SCANNING ELECTROMAGNET EXCITING CURRENT VALUE (Y) | MAIN DOSIMETER PRESET COUNT VALUE A1 | MAIN DOSIMETER PRESET COUNT VALUE A2 | SUB DOSIMETER PRESET COUNT VALUE B1 | SUB DOSIMETER PRESET COUNT VALUE B2 | PRESET COUNT VALUES FOR SECOND ABNORMALITY DETERMINATION A3, B3 |
|---|---|---|---|---|---|---|---|
| 10 | 5 | 5 | 300000 | 3000 | 330000 | 3100 | 1000 |
| 10 | 10 | 5 | 280000 | 3000 | 308000 | 3100 | 1000 |
| 10 | 15 | 10 | 250000 | 3000 | 275000 | 3100 | 1000 |
| 10 | 25 | 10 | 280000 | 3000 | 308000 | 3100 | 1000 |
| 12 | 5 | 5 | 50000 | 3000 | 55000 | 3100 | 500 |
| 12 | 15 | 10 | 51000 | 3000 | 56100 | 3100 | 500 |
| 12 | 20 | 10 | 52000 | 3000 | 57200 | 3100 | 500 |
| 15 | 5 | 15 | 19000 | 3000 | 20900 | 3100 | 100 |
| 15 | 15 | 15 | 20000 | 3000 | 22000 | 3100 | 100 |
| ... | ... | ... | ... | ... | ... | ... | ... |
| 20 | 25 | 25 | 15000 | 300 | 16500 | 310 | 100 |

FIG. 10

PATTERN FILE 40b

| SETTING VALUE OF RANGE SHIFTER THICKNESS | SCANNING ELECTROMAGNET EXCITING CURRENT VALUE (X) | SCANNING ELECTROMAGNET EXCITING CURRENT VALUE (Y) | MAIN DOSIMETER PRESET COUNT VALUE A1 | MAIN DOSIMETER PRESET COUNT VALUE A2 | SUB DOSIMETER PRESET COUNT VALUE B1 | SUB DOSIMETER PRESET COUNT VALUE B2 | PRESET COUNT VALUES FOR SECOND ABNORMALITY DETERMINATION A3, B3 | PRESET COUNT VALUES FOR THIRD ABNORMALITY DETERMINATION A4, B4 |
|---|---|---|---|---|---|---|---|---|
| 10 | 5 | 5 | 300000 | 3000 | 330000 | 3100 | 1000 | 5 |
| 10 | 10 | 5 | 280000 | 3000 | 308000 | 3100 | 1000 | 5 |
| 10 | 15 | 10 | 250000 | 3000 | 275000 | 3100 | 1000 | 5 |
| 10 | 25 | 10 | 280000 | 3000 | 308000 | 3100 | 1000 | 5 |
| 12 | 5 | 5 | 50000 | 3000 | 55000 | 3100 | 500 | 5 |
| 12 | 15 | 10 | 51000 | 3000 | 56100 | 3100 | 500 | 5 |
| 12 | 20 | 10 | 52000 | 3000 | 57200 | 3100 | 500 | 5 |
| 15 | 5 | 15 | 19000 | 3000 | 20900 | 3100 | 100 | 5 |
| 15 | 15 | 15 | 20000 | 3000 | 22000 | 3100 | 100 | 5 |
| . | . | . | . | . | . | . | . | |
| 20 | 25 | 25 | 15000 | 300 | 16500 | 310 | 100 | 5 |

FIG. 14

PARTICLE BEAM IRRADIATION APPARATUS AND CONTROL METHOD OF THE PARTICLE BEAM IRRADIATION APPARATUS

TECHNICAL FIELD

The present invention relates to a particle beam irradiation apparatus and a control method of the particle beam irradiation apparatus, and particularly for directing a heavy particle beam of carbon, a proton beam, or the like to an affected area to treat cancer.

BACKGROUND ART

Today, cancer is the highest cause of death, and more than 300,000 people die of cancer every year. Under the circumstances, a particle radiation therapy using a carbon beam and a proton beam with excellent features of high therapeutic effects and few side effects is drawing attention. In the therapy, a particle beam emitted from an accelerator can be directed to cancer cells to destroy the cancer cells while reducing influence on normal cells.

In the therapeutic method, a currently used particle beam irradiation method is a method called a broad beam method. In the broad beam method, a diameter of the particle beam is expanded to a size greater than the affected area based on a method called a wobbler method or a double scatter method. A brass collimator called a geometric collimator limits an irradiation area to direct the beam in accordance with a shape of the affected area. A beam range expansion apparatus called a ridge filter expands the beam in a beam travelling direction (beam axis direction). A polyethylene beam range shaping apparatus called a compensator adjusts a beam termination position according to a shape (outline) of the affected area at a deep position to direct the beam.

However, the broad beam method is not capable of precise three-dimensional adjustment of the beam in accordance with the shape of the affected area, and there is a limit to reducing the influence on the normal cells around the affected area. The geometric collimator and the compensator are created for each affected area (and for each irradiation direction relative to the affected area), and there is a problem that radioactive wastes are generated after therapeutic irradiation.

Consequently, scanning irradiation for dividing the affected area inside of a body into three-dimensional lattices before irradiation is being developed as a further advanced form of irradiation in the particle beam treatment. In the scanning irradiation, the beam can be accurately adjusted to the affected area in the beam axis direction without using the geometric collimator or the compensator, and exposure to the normal cells can be reduced compared to conventional two-dimensional irradiation.

For example, each point is irradiated as follows in three-dimensional irradiation called spot scanning irradiation.

When a predetermined dose is directed to a point (operation of determining the irradiation dose for each irradiation point is called treatment planning), a scanning control apparatus receives a completion signal from a dosimeter and outputs a spot switch command. A beam emission control apparatus terminates beam emission based on the spot switch command. At the same time, a power supply of a scanning electromagnet starts setting a current value corresponding to coordinates of a next irradiation point. When receiving a completion signal of the current value setting of the electromagnetic power supply, the scanning irradiation apparatus outputs a beam start command to the beam emission control apparatus, and irradiation for the next point is started. This is sequentially repeated to irradiate a treatment region with respect to one irradiation slice (surface). When the irradiation is finished, the beam emission is temporarily terminated. Energy of the beam emitted from the accelerator is changed, or a range adjustment apparatus called a range shifter is controlled to change a beam termination position (slice) in the beam travelling direction. In this way, the scanning irradiation and the slice switch are sequentially performed for irradiation of the entire treatment region.

The particle beam is accumulated in a certain beam energy state, in an accelerator called a synchrotron. At the beam emission, the beam emission control apparatus arranged on a beam extraction port on the accelerator provides a high frequency electric field to the beam to extract the beam to implement the beam in the irradiation apparatus. The beam emission in the spot switch and the slice switch is terminated by terminating the application of the high frequency electric field.

A weak point of the spot scanning irradiation is that the beam emission cannot be actually immediately terminated even if the beam emission control apparatus outputs the beam termination command. Therefore, a leakage dose is directed to the affected area when an exciting current of the electromagnet is changed, i.e. when the irradiation position is moved. This is particularly a problem when the irradiation dose (set dose) for each point is small, because a ratio of the leakage dose (leakage dose/set dose) is large. To prevent the problem, beam intensity needs to be reduced to make the ratio of the leakage dose relatively small. However, the reduction in the beam intensity leads to an increase in the time for treatment, and a physical burden of the patient increases.

A method called a raster scanning method is studied to solve the problem that the beam intensity cannot be increased in the spot scanning method (see Non-Patent Document 1 or the like). In the method, the beam is not terminated when the irradiation point is moved, unlike in the spot scanning method. Therefore, the beam is irradiated when the beam position moves between a termination irradiation position (a point for directing a dose that is set when the irradiation position is terminated, not when the irradiation position is moving, will be called a termination irradiation point) and a termination irradiation point. The treatment planning including an amount of irradiation during the irradiation, i.e. irradiation dose at each termination point, is optimized.

An example of a region as a target of the particle beam treatment includes a region that moves along with respiration, such as lungs and liver. In-gate irradiation is performed for such a region, in which a respiration waveform signal is acquired, and the irradiation is performed only if the region is at a position within a certain range. However, the irradiation points are sequentially switched in the scanning irradiation. Therefore, the irradiation points are relatively deviated along with the movement of the region caused by respiration, and a dose distribution becomes non-uniform. To solve this, Non-Patent Document 1 proposes following respiration-synchronized irradiation.

In the respiration-synchronized irradiation, the beam intensity is set so that one irradiation time in one slice (time for one irradiation of the entire irradiation area in the target slice) becomes 1/n of a gate width of one respiration. Repeated irradiation is performed for n times (for example, n=eight ties) during one respiration. When the irradiation in the target slice is finished, the irradiation slice is changed, and the beam intensity for a next irradiation slice is reset to perform the irradiation in the slice.

In this way, the irradiation time control (called phase control in Non-Patent Document 1) and the repeated irradiation (called re-scanning in Non-Patent Document 1) within one slice can be performed to disperse the irradiation area with respect to the movement of the region, and the dose uniformity can be improved in accordance with a statistical error $1/\sqrt{n}$.

CITATION LIST

Non-Patent Document

Non-Patent Document 1: Takuji Furukawa and eight others, "Design Study of Three-Dimensional Scanning Irradiation Apparatus", National Institute of Radiological Sciences HIMAC Report: HIMAC-124, issued by National Institute of Radiological Sciences, April 2007.

SUMMARY OF INVENTION

Technical Problem

When normal irradiation may not be able to be performed after generation of an abnormality in a device of an irradiation apparatus, a particle beam treatment apparatus requires an interlock mechanism for immediately recognizing this to terminate the beam emission.

For example, a scanning irradiation apparatus usually includes two dosimeters (a main dosimeter and a sub dosimeter). When a dose measured by the main dosimeter at a beam position reaches a predetermined reference dose, the scanning irradiation apparatus executes a process of outputting a dose completion signal to change the beam position. The scanning irradiation apparatus also compares the dose of each spot measured by the main/sub dosimeters with predetermined reference values (preset values) of the main/sub dosimeters to always confirm normal operations of the apparatus. When there is an abnormality in one of the main/sub dosimeters, the scanning irradiation apparatus generates an interlock signal to terminate the beam emission.

Another example of abnormality generated in the scanning irradiation apparatus includes an abnormality that the beam is emitted, in spite of the fact that the beam emission is set to a termination state during slice switching. The abnormality occurs when, for example, electric noise enters the beam emission apparatus, and there is unintended beam emission due to the electric noise. Providing of a dose caused by the unintended beam emission is called a leakage dose. The leakage dose is monitored by, for example, accumulating and measuring the number of pulses of a pulse signal output from the main dosimeter during a beam termination period.

However, the inventors have studied the raster scanning irradiation apparatus, and as a result, it has become apparent that the monitoring method is not sufficient.

For example, high voltage power supplies are connected to the main/sub dosimeters, and outputs of the high voltage power supplies may be turned off due to an operation error or the like in an actual therapeutic scene. If the irradiation is started when the high voltage power supplies of the main/sub dosimeters are forgotten to be turned on, there is no output from the main/sub dosimeters, and a signal indicating completion of the dose cannot be output from the measurement values of the main/sub dosimeters. Therefore, excessive irradiation may occur.

A current abnormality determination logic is a logic of determining presence/absence of abnormality in the main/sub dosimeters when measurement dose values output from the main/sub dosimeters reach preset values allocated to each spot. Therefore, the abnormality cannot be determined according to the abnormality determination logic, until the completion of the irradiation of the spot.

As for the leakage dose, sufficient measurement sensitivity cannot be attained. The time of a malfunction in the beam emission apparatus caused by noise or the like is about 0.1 msec, while the time that the beam emission needs to be terminated in the respiration-synchronized irradiation is one to two seconds (during inhale of respiration). Therefore, assuming that a dosimeter output during beam emission is S (signal) and a dosimeter output during termination is N (noise), four digits are necessary for S/N of the dosimeter. Such sensitivity in the dosimeter is actually difficult to attain. Therefore, even if there is a leakage dose in respiration-synchronized beam-off time, the leakage dose is buried in the accumulation measurement value of noise, and the leakage dose cannot be identified.

The present invention has been made in view of the circumstances, and an object of the present invention is to provide a particle beam irradiation apparatus and a control method of the particle beam irradiation apparatus capable of highly reliable measurement of a dose of each beam and capable of highly sensitive measurement of a leakage dose caused by momentary beam emission.

Solution to Problems

To solve the problems, the present invention provides a particle beam irradiation apparatus that directs a particle beam to an affected area of a patient, the particle beam irradiation apparatus comprising: an emission control portion that controls emission and termination of the particle beam; a control portion that sequentially changes an irradiation position of the particle beam for the affected area; first and second dosimeters that measure dose rates of the particle beam directed to the affected area; and an abnormality determination portion that uses dose measurement values obtained by accumulating the dose rates output from the first and second dosimeters to perform abnormality determination of the apparatus and that outputs, to the emission control portion, an interlock signal for terminating the emission of the particle beam when determining that there is an abnormality, wherein the control portion accumulates the dose rate output from the first dosimeter for each of irradiation positions of the particle beam to calculate a first beam dose measurement value and changes the irradiation position of the particle beam when the first beam dose measurement value reaches a first planned dose value predetermined for each of the irradiation positions, and the abnormality determination portion performs: first abnormality determination of accumulating the dose rate output from the second dosimeter for each of the irradiation positions of the particle beam to calculate a second beam dose measurement value and determining that there is the abnormality if the calculated second beam dose measurement value exceeds a second planned dose value that is set to a value greater than the first planned dose value or if a ratio of the second beam dose measurement value relative to the second planned dose value when the first beam dose measurement value reaches the first planned dose value is smaller than a predetermined ratio; and second abnormality determination of accumulating the dose rates output from the first and second dosimeters for each of predetermined determination periods to calculate first and second sectional dose measurement values and determining that there is the abnormality in at least one of a case in which the first sectional dose measurement value exceeds a predetermined first reference range and a case in which the second sectional dose measurement value exceeds a predetermined second reference range.

The present invention provides a control method of a particle beam irradiation apparatus that directs a particle beam to an affected area of a patient, the control method comprising the steps of: controlling emission and termination of the particle beam; sequentially changing an irradiation position of the particle beam for the affected area; measuring, by first and second dosimeters, dose rates of the particle beam directed to the affected area; performing abnormality determination of the apparatus using dose measurement values obtained by accumulating the dose rates output from the first and second dosimeters; and terminating the emission of the particle beam using an interlock signal when determining that there is an abnormality, wherein in the step of changing the irradiation position of the particle beam, the dose rate output from the first dosimeter is accumulated for each of irradiation positions of the particle beam to calculate a first beam dose measurement value, and the irradiation position of the particle beam is changed when the first beam dose measurement value reaches a first planned dose value predetermined for each of the irradiation positions, and the step of performing the abnormality determination includes: performing first abnormality determination of accumulating the dose rate output from the second dosimeter for each of the irradiation positions of the particle beam to calculate a second beam dose measurement value and determining that there is the abnormality if the calculated second beam dose measurement value exceeds a second planned dose value that is set to a value greater than the first planned dose value or if a ratio of the second beam dose measurement value relative to the second planned dose value when the first beam dose measurement value reaches the first planned dose value is smaller than a predetermined ratio; and performing second abnormality determination of accumulating the dose rates output from the first and second dosimeters for each of predetermined determination periods to calculate first and second sectional dose measurement values and determining that there is the abnormality in at least one of a case in which the first sectional dose measurement value exceeds a predetermined first reference range and a case in which the second sectional dose measurement value exceeds a predetermined second reference range.

Advantageous Effects of Invention

According to the particle beam irradiation apparatus and the control method of the particle beam irradiation apparatus of the present invention, highly reliable measurement of a dose of each beam is possible, and highly sensitive measurement of a leakage dose caused by momentary beam emission is possible.

BRIEF DESCRIPTION OF THE DRAWINGS

FIG. 5 is a diagram showing an example of an irradiation pattern file used in conventional abnormality determination.

FIG. 10 is a diagram showing an example of an irradiation pattern file used in the first embodiment.

FIG. 14 is a diagram showing an example of an irradiation pattern file used in the third embodiment.

DESCRIPTION OF EMBODIMENTS

Embodiments of a particle beam irradiation apparatus and a control method of the particle beam irradiation apparatus according to the present invention will be described with reference to the attached drawings.

(1) Configuration and Basic Operation

Figure 1:
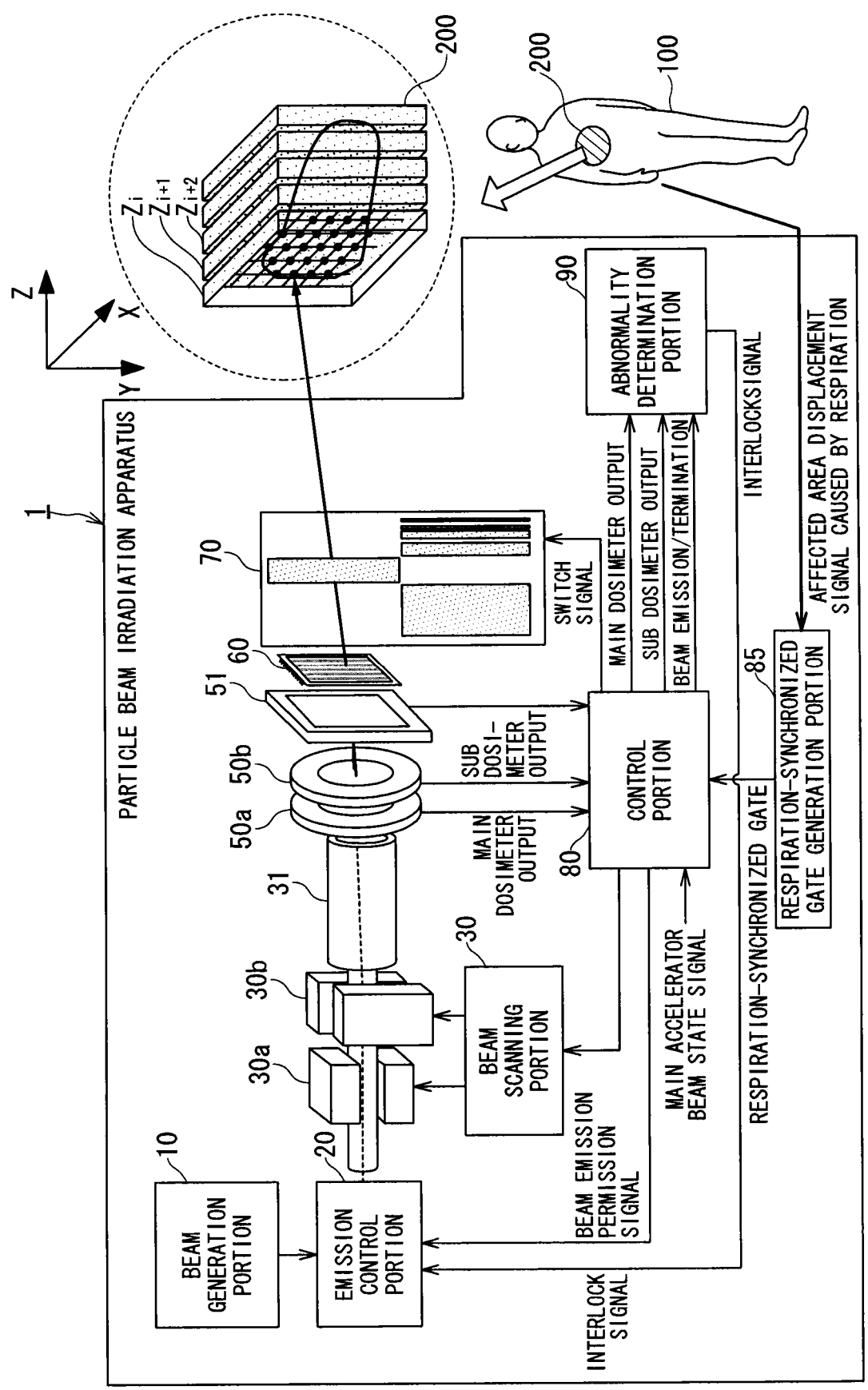
FIG. 1 is a diagram showing an example of configuration of a particle beam irradiation apparatus.

FIG. 1 is a diagram showing an example of configuration of a particle beam irradiation apparatus 1 according to a first embodiment. The particle beam irradiation apparatus 1 includes a beam generation portion 10, an emission control portion 20, a beam scanning portion 30, an X electromagnet 30$a$, a Y electromagnet 30$b$, a vacuum duct 31, a main dosimeter (first dosimeter) 50$a$, a sub dosimeter (second dosimeter) 50$b$, a position monitoring portion 51, a ridge filter 60, a range shifter 70, a control portion 80, an abnormality determination portion 90, and the like.

The particle beam irradiation apparatus 1 is an apparatus that directs a particle beam, which is obtained by accelerating particles of carbon, protons, or the like to high speed, toward an affected area 200 of a cancer patient 100 to treat cancer. The particle beam irradiation apparatus 1 can carry out three-dimensional scanning irradiation of breaking up the affected area 200 into three-dimensional lattice points and sequentially scanning the lattice points by a particle beam with a small diameter. Specifically, the particle beam irradiation apparatus 1 divides the affected area 200 into plates called slices in an axial direction of the particle beam (Z-axis direction in a coordinate system shown in the upper right of FIG. 1) and sequentially scans two-dimensional lattice points of the divided slices, such as a slice $Z_i$, a slice $Z_{i+1}$, and a slice $Z_{i+2}$ (lattice points in X-axis and Y-axis directions in the coordinate system shown in the upper right of FIG. 1), to thereby perform three-dimensional scanning.

The beam generation portion 10 generates a particle beam by generating particles, such as carbon ions and protons, and using an accelerator (main accelerator), such as a synchrotron, to accelerate the particles up to energy that allows reaching deep in the affected area 200.

The emission control portion 20 controls on/off of emission of the generated particle beam based on a control signal output from the control portion 80.

The beam scanning portion 30 is configured to deflect the particle beam in an X direction and a Y direction and to two-dimensionally scan a slice surface. The beam scanning portion 30 controls exciting currents of the X electromagnet 30a for scan in the X direction and the Y electromagnet 30b for scan in the Y direction.

The range shifter 70 controls a position of the affected area 200 in the Z axis direction. The range shifter 70 includes, for example, a plurality of acrylic plates in different thicknesses. The acrylic plates can be combined to gradually change energy, i.e. an internal range, of the particle beam passing through the range shifter 70 according to a position of the slice of the affected area 200 in the Z-axis direction. A size of the internal range based on the range shifter 70 is usually controlled to change at an equal distance, and the interval is equivalent to an interval between the lattice points in the Z-axis direction. Examples of a method of switching the internal range include a method of inserting an attenuation object on a path of the particle beam as in the range shifter 70 and a method of changing the energy of the particle beam based on control of an upstream device.

The ridge filter 60 is arranged to spread a sharp peak of a dose in a depth direction inside of the body called a Bragg peak. A spreading width of the Bragg peak based on the ridge filter 60 is set to be equal to the thickness of the slice, i.e. the interval between the lattice points in the Z-axis direction. The ridge filter 60 for three-dimensional scanning irradiation is formed by arranging a plurality of aluminum rod-like members with a substantially isosceles triangle shape in cross section. The peak of the Bragg peak can be spread based on a difference between path lengths generated when the particle beam passes through the isosceles triangles. The spreading width can be set to a desired value based on shapes of the isosceles triangles.

The main dosimeter 50a and the sub dosimeter 50b are configured to monitor an irradiated dose. Each casing of the main dosimeter 50a and the sub dosimeter 50b includes: an ionization chamber including parallel electrodes that collect charge generated by ionization of the particle beam; and an SEM (Secondary Electron Monitor) apparatus that measures secondary electrons emitted from a secondary electron emission film arranged in the casing.

The position monitoring portion 51 is configured to identify whether the particle beam scanned by the beam scanning portion 30 is at a correct position. The position monitoring portion 51 includes parallel electrodes for charge collection similar to those of the main dosimeter 50a and the sub dosimeter 50b. The electrodes for charge collection of the position monitoring portion 51 include linear electrodes (for example, a plurality of strip-shaped electrodes or electrodes made of a plurality of wires) aligned in parallel in the X direction and the Y direction. The plurality of aligned strip electrodes are called strip type electrodes, and the plurality of aligned wire electrodes are called multi-wire type electrodes.

The control portion 80 is configured to control the entire particle beam irradiation apparatus 1. The control portion 80 controls on/off of the beam emission for the emission control portion 20, issues an instruction related to beam scanning to the beam scanning portion 30, and controls an amount of range shift of the range shifter 70 associated with a slice change.

The respiration-synchronized gate generation portion 85 generates a respiration-synchronized gate from an affected area displacement signal output from a displacement sensor installed near the affected area 200. The respiration-synchronized gate is used to direct a particle beam to an affected area that is displaced by respiration, such as lungs and liver. If the displacement of the affected area is greater than a predetermined value, the respiration-synchronized gate is turned off to terminate the emission of the particle beam. If the displacement of the affected area is smaller than a predetermined value, the respiration-synchronized gate is turned on to emit the particle beam.

The abnormality determination portion 90 imports output signals of the main dosimeter 50a and the sub dosimeter 50b as well as a signal indicating a beam emission condition, and based on the signals, performs abnormality determination of the dose of the particle beam directed to the patient. If the dose is determined to be abnormal, the interlock signal is immediately output to the emission control portion 20, and the emission of the particle beam is terminated.

The particle beam irradiation apparatus 1 according to the present embodiment is characterized by the configuration and processing by the abnormality determination portion 90, and abnormality determination is performed with higher reliability than in the conventional technique. A specific abnormality determination process will be described later.

Figure 2:
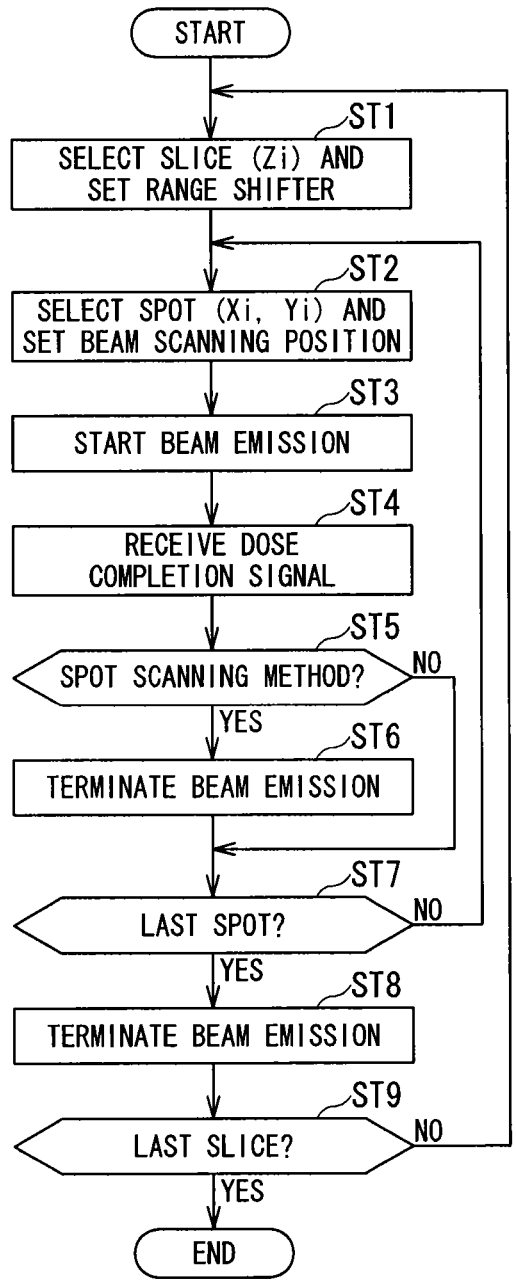
FIG. 2 is a flow chart showing an example of basic processing of three-dimensional scanning irradiation.

FIG. 2 is a flow chart showing an example of basic processing of three-dimensional scanning irradiation performed by the particle beam irradiation apparatus 1.

The affected area is virtually divided into a plurality of slices relative to the beam axis, and one of the divided slices is selected. For example, a slice Zi at a deepest position of the affected area is first selected. Incident energy of the particle beam and a combination of the acrylic plates in the range shifter 70 are selected and set according to the position of the selected slice (step ST1).

The number M of lattice points to be irradiated by the particle beam and a position of a lattice point (Xi, Yi) [i=1 to M], i.e. a spot to be irradiated, are selected according to the shape of the affected area in the deepest slice, and the beam scanning portion 30 sets a direction of the particle beam to the lattice point position (Xi, Yi) (step ST2) on the slice. The emission of the particle beam is started (step ST3). The ridge filter 60 expands an energy distribution of the particle beam in the Z-axis direction so that an internal range distribution width corresponds to a slice width.

The main dosimeter 50a and the sub dosimeter 50b monitor the irradiation dose for the lattice point (Xi, Yi). The main dosimeter 50a and the sub dosimeter 50b output pulse signals with a pulse repetition frequency proportional to a dose rate of the passing particle beam. A counter can count the number of pulses in a predetermined period to measure the dose in the predetermined period.

Although the main dosimeter 50a and the sub dosimeter 50b usually have the same configuration, the configuration is not necessarily limited to the same configuration. If the main dosimeter 50a and the sub dosimeter 50b have different configurations, measurement values, such as the number of output pulses, can be corrected in advance so that a measurement value of a same physical quantity (dose rate) can be obtained for a same particle beam.

The irradiation dose for each lattice point in the slice is planned in advance. When the number of pulses output from the main dosimeter 50a is counted to measure the dose, and the irradiation dose for a target lattice point reaches a planned dose, a dose completion signal is generated. When the control portion 80 detects the signal (step ST4), the control portion 80 executes a process of changing the beam position. Although the control portion 80 generates the dose completion signal, the main dosimeter 50a may generate the dose completion signal.

The three-dimensional scanning irradiation is classified into a spot scanning method and a raster scanning method. The spot scanning method is a method of terminating the beam emission when the position of the particle beam is being moved from a lattice point to a next lattice point and restarting the beam emission after the completion of the movement. Therefore, the beam emission is intermittent during the scan of a slice.

On the other hand, in the raster scanning method, the beam emission is continued without being terminated when the position of the particle beam is being moved from a lattice point to a next lattice point. Therefore, the beam emission is continued without being interrupted during the scan of a slice.

In both the spot scanning method and the raster scanning method, the position of the particle beam is remained until the dose reaches a dose planned in each lattice point, and the position moves to the next lattice point after the dose reaches the planned dose.

In step ST5, whether the method is the spot scanning method or the raster scanning method is determined. If the method is the spot scanning method, the beam emission is temporarily terminated (step ST6), and the beam position is moved to the next spot. The process is repeated up to a last spot of the target slice (step ST7).

On the other hand, if the method is not the spot scanning method, i.e. if the method is the raster scanning method, the beam emission is continued up to the last spot without terminating the beam emission.

When the irradiation of one slice is finished (YES in step ST7), the beam emission is temporarily terminated both in the spot scanning method and the raster scanning method (step ST8), and the process returns to step ST1. A next slice is selected, and setting of the range shifter 70 is changed. The process is repeated up to the last slice (step ST9).

Parameters necessary for the irradiation procedure are described in, for example, a data file called an irradiation pattern file (hereinafter, may be simply called "pattern file"), and the parameters are transferred to the control portion 80 before the start of the therapeutic irradiation. The irradiation pattern file describes, for each lattice point, a range shifter thickness for providing the slice position, drive current values of the X electromagnet 30a and the Y electromagnet 30b for providing the beam position corresponding to the lattice point (X,Y), an irradiation dose for the lattice point, and the like, in the order of irradiation.

Figure 3:
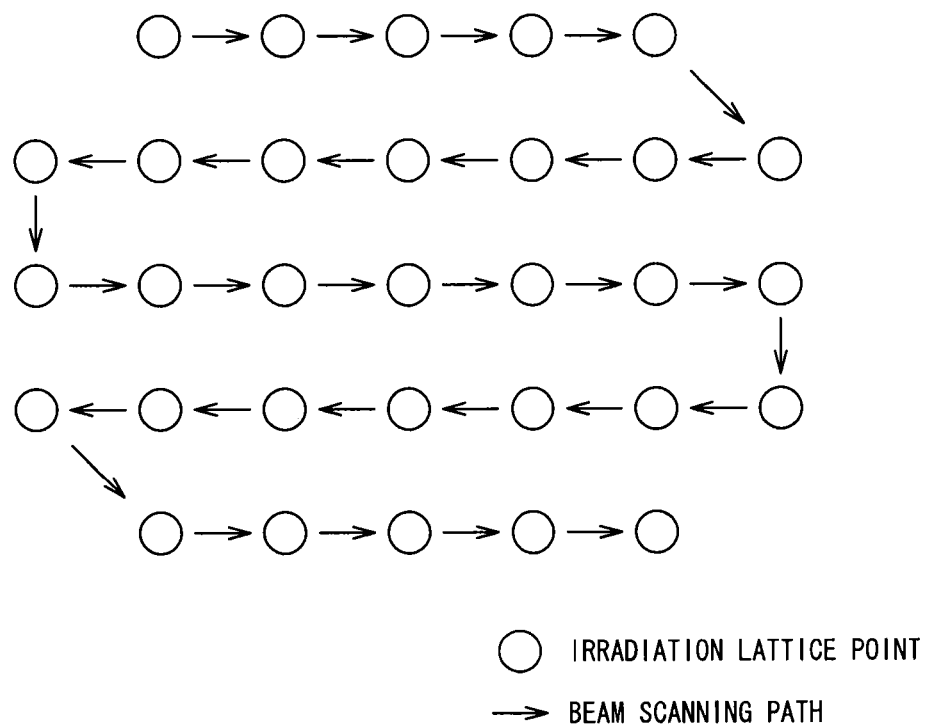
FIG. 3 is a diagram showing an example of a scan pattern on a slice.

FIG. 3 is a diagram showing an example of a scan pattern on a slice. A trajectory pattern from a start lattice point on the upper left to a final lattice point on the lower right is predetermined in the treatment planning, and the particle beam is sequentially scanned in one way along the trajectory pattern.

(2) Conventional Particle Beam Irradiation Method and Abnormality Determination Method (Example of Comparison)

A conventional abnormality determination method will be described as an example of comparison of the abnormality determination method of the particle beam irradiation apparatus 1 according to the present embodiment.

Figure 4:
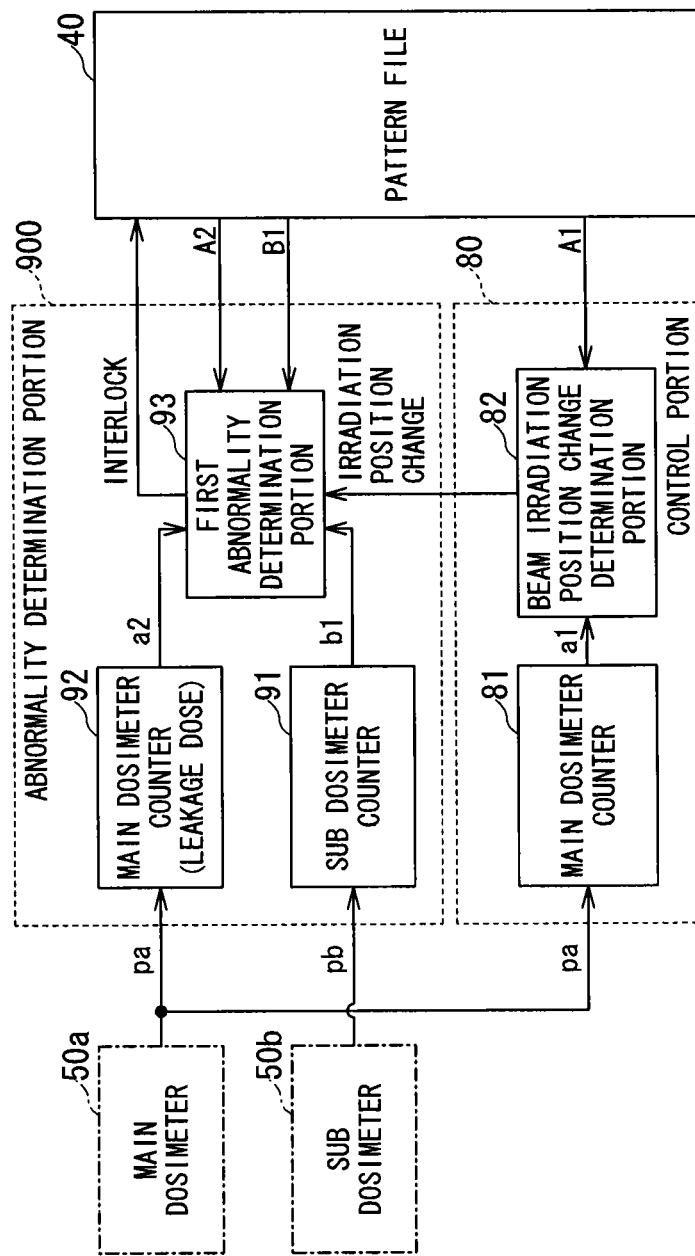
FIG. 4 is a diagram showing an example of configuration of a conventional abnormality determination portion.

FIG. 4 is a block diagram showing functional blocks of the control portion 80 related to the changing process of the particle beam position and functional blocks related to a conventionally executed abnormality determination (first abnormality determination) process.

The irradiation procedure is described in an irradiation pattern file 40, and the irradiation is performed according to pattern data described in the file 40. The pattern data is set in the particle beam irradiation apparatus 1 before the start of the therapeutic irradiation.

FIG. 5 is a diagram showing an example of the irradiation pattern file 40. The irradiation pattern file 40 describes, for each irradiation point (spot), a setting value of range shifter thickness for providing the irradiation slice position, scanning electromagnetic exciting current values (two values for X and Y) for providing the irradiation position (X, Y), a setting value for the main dosimeter 50a to manage the dose during the beam emission (main dosimeter preset count value A1: first planned dose value), a setting value for the main dosimeter 50a to monitor the dose (leakage dose) during the beam termination (main dosimeter preset count value A2), a setting value for the sub dosimeter 50b to monitor the dose during the beam emission (sub dosimeter preset count value B1: second beam dose planned value), a setting value for the sub dosimeter 50b to monitor the dose (leakage dose) during the beam termination (sub dosimeter preset count value B2), and the like.

Figure 6:
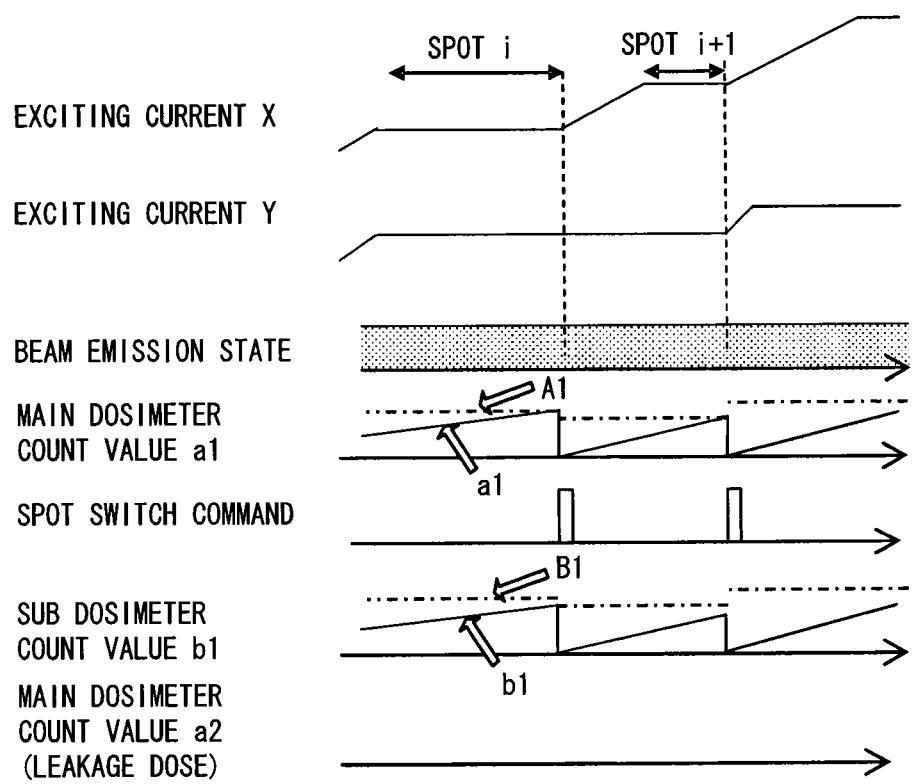
FIG. 6 is a first timing chart showing a state of conventional control and management of an irradiation dose.

FIG. 6 is a timing chart showing a state of control and management of the irradiation dose in the raster scanning irradiation. A main dosimeter counter 81 of the control portion 80 counts the number of pulses output from the main dosimeter 50a. When an integrated count value a1 (first beam dose measurement value) reaches the setting value (main dosimeter preset count value A1), a beam irradiation position change determination portion 82 of the control portion 80 outputs a spot switch command (command for changing the beam irradiation position). A scanning magnet power supply changes a current based on the spot switch command. The beam irradiation point moves according to the current of the power supply, i.e. a change in the magnetic field of the scanning magnet. In the raster scanning irradiation, the emission of the beam is not terminated during the change in the current of the power supply. Therefore, when the count value a1 reaches the main dosimeter preset count value A1, the main dosimeter counter 81 immediately resets the count value and starts the next count.

Meanwhile, the pulse signal output from the sub dosimeter 50b is input to a sub dosimeter counter 91 of an abnormality determination portion 900. The sub dosimeter counter 91 counts the pulses output from the sub dosimeter 50b and transmits a count value b1 (second beam dose measurement value) to a first abnormality determination portion 93. The sub dosimeter preset count value B1 of the irradiation pattern file 40 is usually 5 to 10% higher than the setting value of the main dosimeter 50a (main dosimeter preset count value A1) as illustrated in FIG. 5. Therefore, as long as the main dosimeter 50a and the main dosimeter counter 81 for the main dosimeter are in normal operation, the count value b1 of the sub dosimeter counter 91 does not reach the sub dosimeter preset count B1 when the count value a1 of the main dosimeter counter 81 reaches the main dosimeter preset count value A1. However, if normal output is not performed due to an abnormality in the main dosimeter 50a, or if there is an abnormality in the main dosimeter counter 81, the count value b1 of the sub dosimeter counter 91 reaches the sub dosimeter preset count B1. In this case, the first abnormality determination portion 93 determines that there is an abnormality and outputs an interlock signal to terminate the beam emission.

Just before the switch of the spot, the first abnormality determination portion 93 can compare the count value b1 of the sub dosimeter counter 91 with the value of the sub dosimeter preset count B1. If the ratio between the values is smaller than a certain ratio (ratio of 1 or less), the first abnormality determination portion 93 can determine that there is an abnormality in the sub dosimeter 50b or the sub dosimeter counter 91 and can output the interlock to terminate the beam emission.

However, when both the main dosimeter 50a and the sub dosimeter 50b are in an abnormal state, or for example, when the high voltage power supplies of the main dosimeter 50a and the sub dosimeter 50b are not in a voltage output state, the main/sub dosimeters 50a and 50b do not output signals based only on the conventional abnormality determination performed by the first abnormality determination portion 93. Therefore, the count value a1 of the main dosimeter counter 81 and the count value b1 of the sub dosimeter counter 91 do not reach the preset count values A1 and B1, respectively, even if the beam emission is started. The dose completion signal and the interlock signal are not output, and excessive irradiation occurs.

Figure 7:
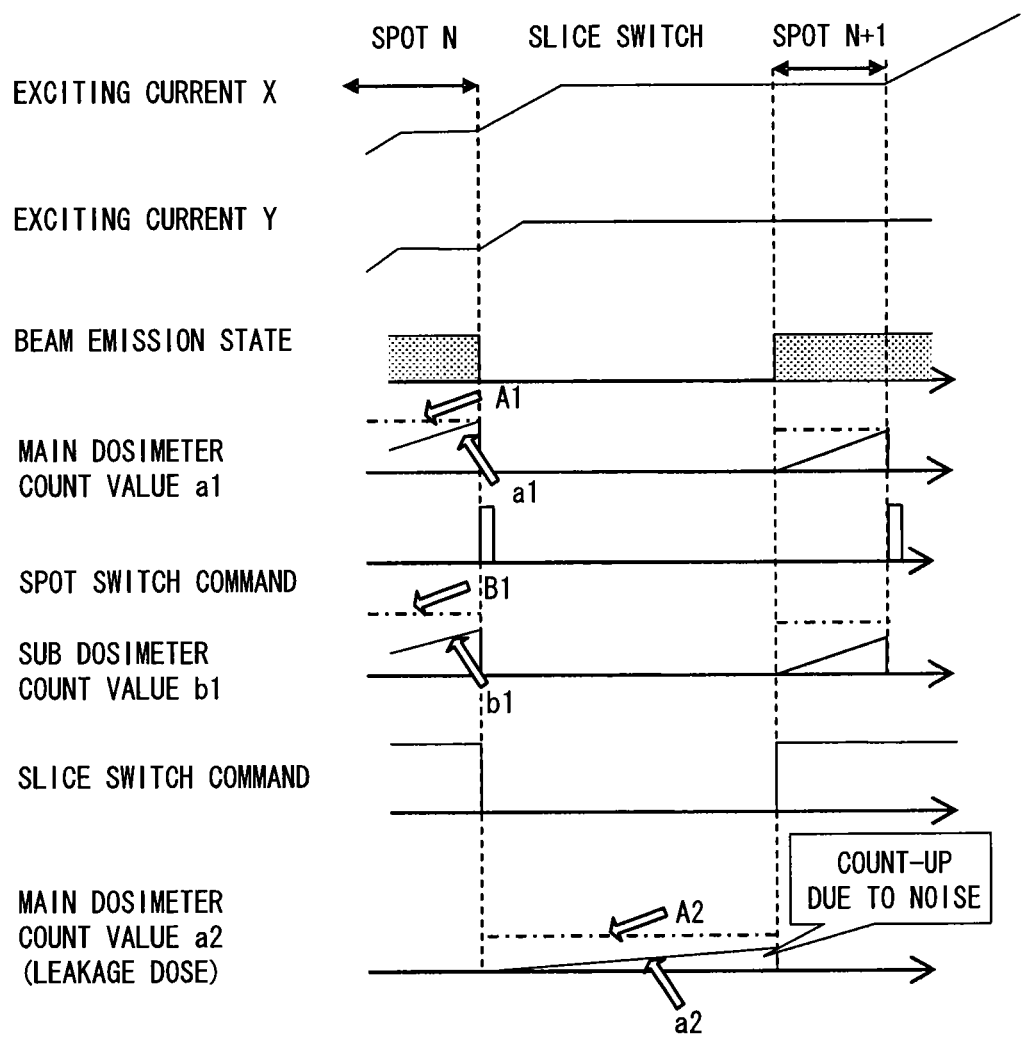
FIG. 7 is a second timing chart showing a state of conventional control and management of the irradiation dose.

FIG. 7 is a timing chart describing a state of conventional control and management of the irradiation dose during the slice switch. When the count value a1 of the main dosimeter counter 81 reaches the preset count A1 at a spot just before the slice switch, the control portion 80 outputs a slice switch command to the range shifter 70 and outputs a control signal for terminating the beam emission to the emission control portion 20. When the beam emission is terminated, the main dosimeter counter 81 of the control portion 80 terminates (resets) the integration.

On the other hand, a main dosimeter counter (for leakage dose) 92 of the abnormality determination portion 900 starts the integration when the beam emission is terminated. The main dosimeter counter (for leakage dose) 92 continues a count-up operation until receiving a slice switch completion signal. When the slice switch completion signal is received, the abnormality determination portion 900 resets the main dosimeter counter (for leakage dose) 92.

The main dosimeter counter 81 of the control portion 80 starts the integration based on the slice switch completion signal and outputs a beam emission start command to the emission control portion 20.

The first abnormality determination portion 93 determines that there is a leakage dose and outputs an interlock to prohibit the beam emission, when a count value a2 of the main dosimeter counter (for leakage dose) 92 exceeds the preset count A2 in a beam emission termination period based on the slice switch. The sub dosimeter also monitors the dose by a similar mechanism. When a count value b2 of a sub dosimeter counter (for leakage dose) (not shown) exceeds the preset count B2 during the termination of the beam emission, the sub dosimeter determines that there is a leakage dose and outputs an interlock to prohibit the beam emission.

Figure 8:
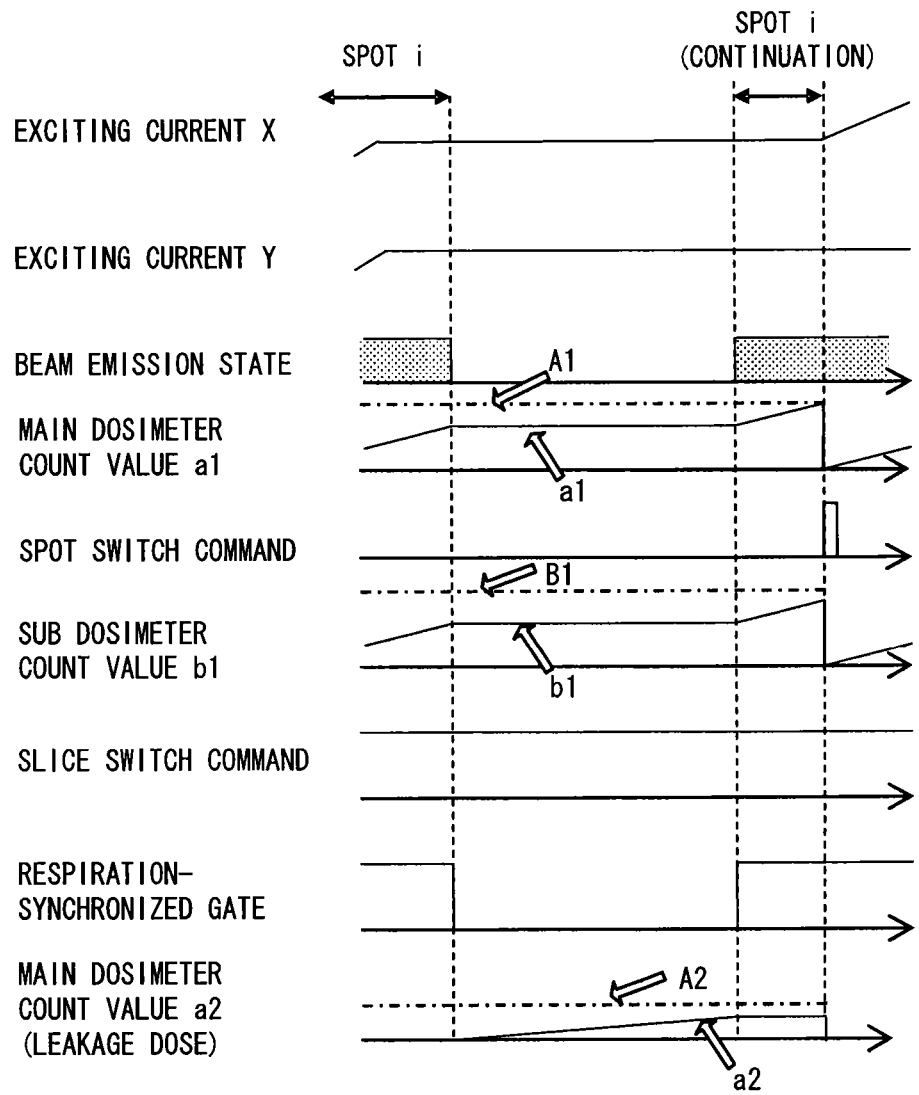
FIG. 8 is a third timing chart showing a state of conventional control and management of the irradiation dose.

FIG. 8 is a timing chart describing a state of control and management of the irradiation dose when the beam emission is terminated by the respiration-synchronized gate. When the respiration-synchronized gate is turned off, the beam emission is terminated even during the spot irradiation. In this case, the main dosimeter counter 81 and the sub dosimeter counter 91 cease the count-up operations while holding the count values a1 and b1, respectively. On the other hand, the main dosimeter (for leakage dose) counter 92 starts the integration when the respiration-synchronized gate is turned off and outputs the count value a2. The state continues until the respiration-synchronized gate is turned on again. When the respiration-synchronized gate is turned on, the integration of the main dosimeter (for leakage dose) counter 92 is terminated, and the integration of the main dosimeter counter 81 and the sub dosimeter counter 91 is restarted.

The first abnormality determination portion 93 determines that there is a leakage dose when the count value a2 of the main dosimeter (for leakage dose) counter 92 exceeds the preset count A2 in the period in which the respiration-synchronized gate is turned off. The first abnormality determination portion 93 generates an interlock signal and prohibits the beam emission. The sub dosimeter also monitors the dose by a similar mechanism. When the count value b2 of the sub dosimeter counter (for leakage dose) (not shown) exceeds the preset count B2 during the termination of the beam emission, the sub dosimeter determines that there is a leakage dose and outputs an interlock to prohibit the beam emission.

Time of the termination of the beam emission caused by the range switch is usually about 0.5 second, and time of the termination of the beam emission caused by the respiration-synchronized gate is about one to two seconds. Spike-like false emission occurs when the emission control portion 20 or the like malfunctions due to noise or the like. A time width of the generation of the leakage dose caused by the false emission is about 0.1 msec.

Meanwhile, low-level noise is constantly generated inside of the main dosimeter 50a (the same applies to the sub dosimeter 50b). Therefore, even if the peak intensity of the spike-like leakage dose is about 10000 times (1 sec/0.1 msec) higher than a level of the internal noise of the main dosimeter 50a, an amount of internal noise (time integral value) integrated in the termination period of the beam emission becomes equivalent to the leakage dose. This means that the main dosimeter (for leakage dose) counter 92 cannot correctly detect the leakage dose if the intensity of the leakage dose is less than 10000 times the level of the internal noise generated in the main dosimeter 50a.

To improve the problem of the conventional abnormality determination method, the particle beam irradiation apparatus 1 according to the present embodiment carries out not only the first abnormality determination, but also second abnormality determination that is a different type, in addition to the first abnormality determination.

(3) First Embodiment

Second Abnormality Determination (Part 1)

Figure 9:
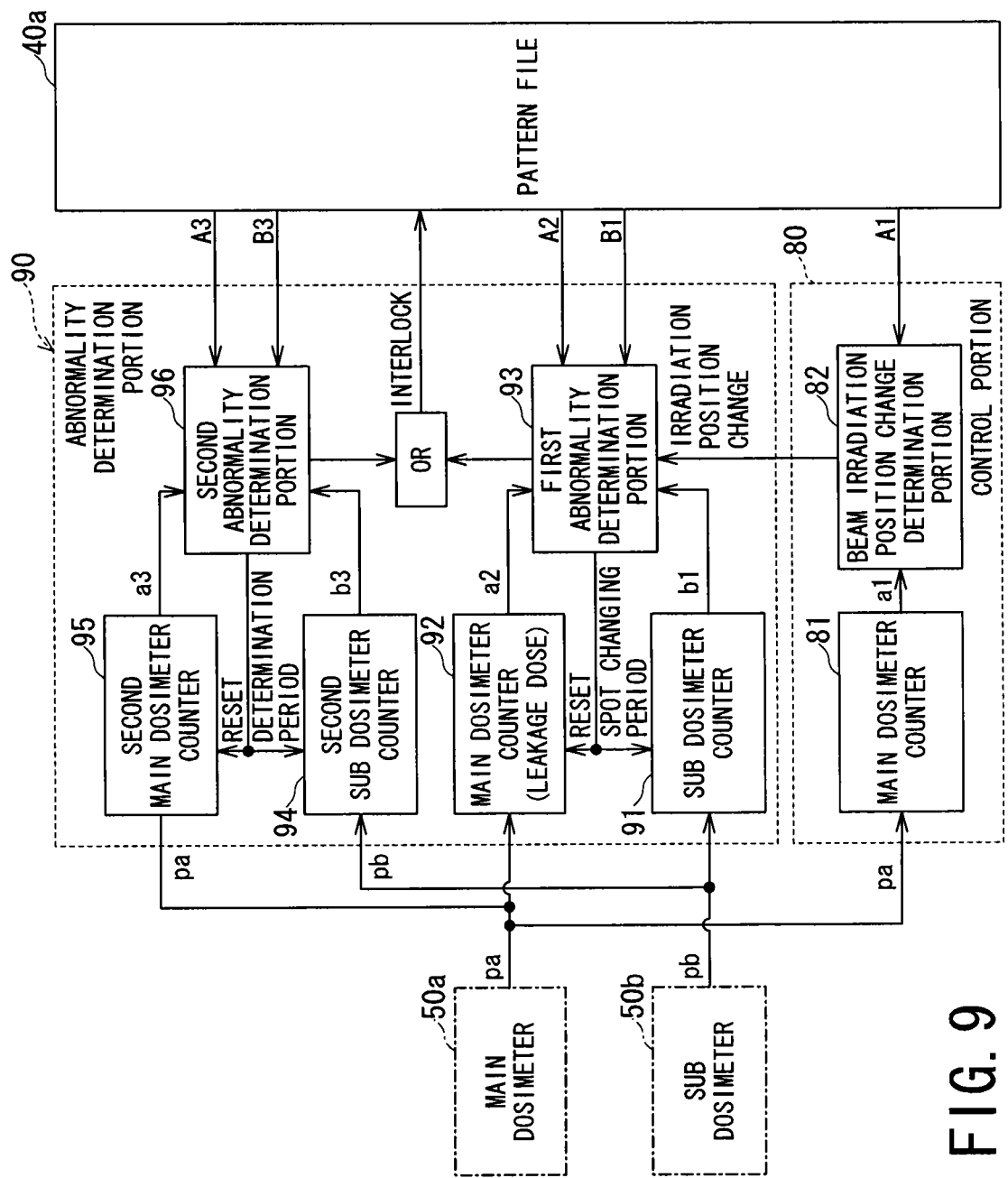
FIG. 9 is a diagram showing an example of configuration of an abnormality determination portion according to a first embodiment.

FIG. 9 is a block diagram mainly showing an example of configuration of the abnormality determination portion 90 according to the first embodiment. The abnormality determination portion 90 according to the first embodiment includes a second main dosimeter counter 95, a second sub dosimeter counter 94, and a second abnormality determination portion 96, in addition to the configuration of the conventional abnormality determination portion 900 (FIG. 4).

Although the second main dosimeter counter 95 counts the number of pulses output from the main dosimeter 50a during the beam emission as in the main dosimeter counter 81, the integration period of the counter is smaller than that of the main dosimeter counter 81.

Although the second sub dosimeter counter 94 counts the number of pulses output from the sub dosimeter 50b during the beam emission as in the sub dosimeter counter 91, the integration period of the counter is smaller than that of the sub dosimeter counter 91.

A count value a3 (first sectional dose measurement value) output from the second main dosimeter counter 95 and a count value b3 (second sectional dose measurement value) output from the second sub dosimeter counter 94 are input to the second abnormality determination portion 96.

Meanwhile, in a pattern file 40a used in the first embodiment, preset count values A3 and B3 for second abnormality determination are added to the data (FIG. 5) of the conventional pattern file 40 as shown in FIG. 10. The preset count values A3 and B3 for second abnormality determination are for determining normal/abnormal of the count values a3 and b3 of the number of pulses output from the main dosimeter 50a and the sub dosimeter 50b during the beam emission. The second abnormality determination portion 96 determines that the count values a3 and b3 of the number of pulses are normal if the count values a3 and b3 are within predetermined determination ranges (first and second reference ranges) defined by upper limits and lower limits obtained based on the preset count values A3 and B3 and determines that the count values a3 and b3 are abnormal if the count values a3 and b3 are out of the determination ranges. In place of the preset count values A3 and B3, the upper limits and the lower limits for setting the determination ranges may be separately defined.

If at least one of the second abnormality determination portion 96 and the first abnormality determination portion 93 determines that there is an abnormality, the interlock signal is output to the emission control portion 20, and the beam emission is terminated.

Figure 11:
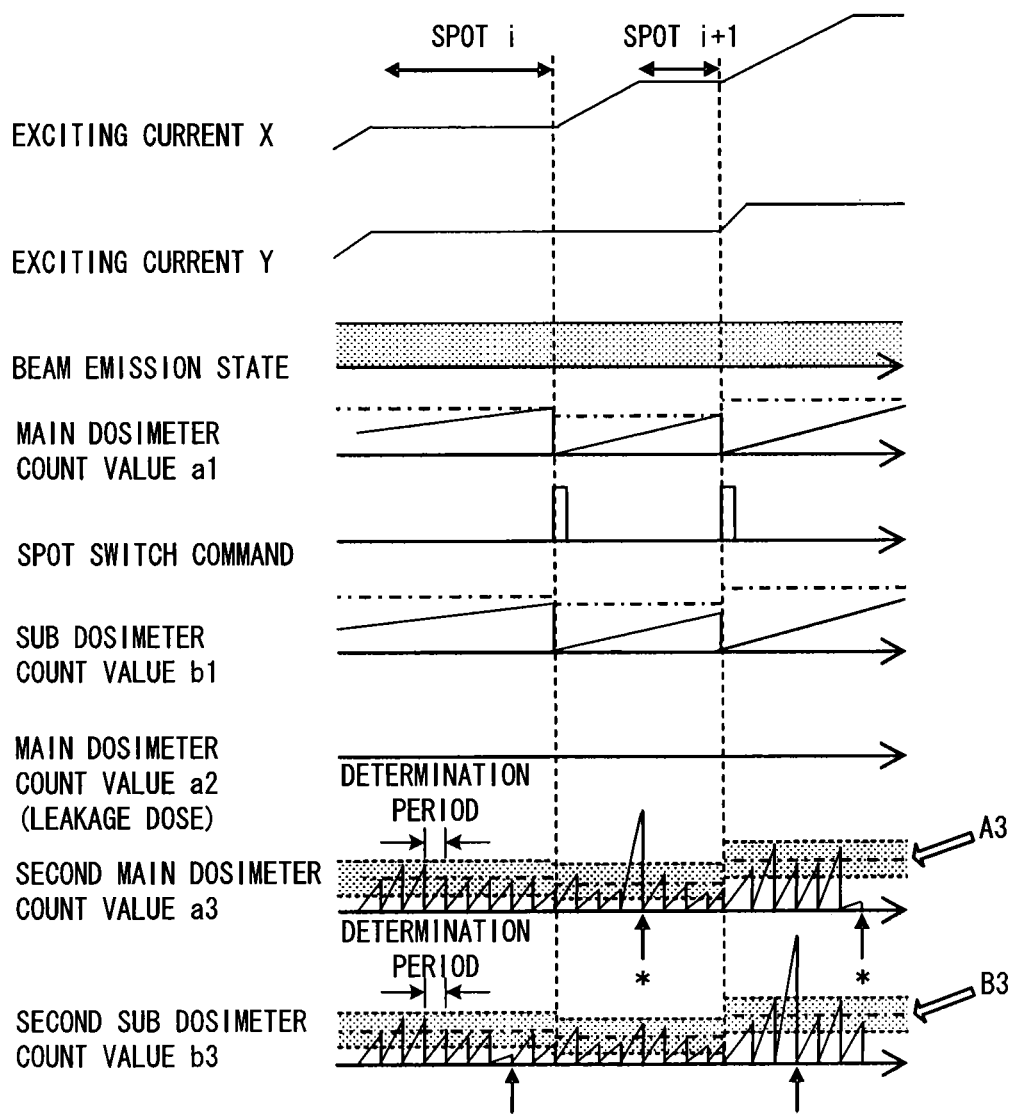
FIG. 11 is a timing chart showing a state of control and management of the irradiation dose according to the first embodiment.

FIG. 11 is a timing chart showing a state of control and management of the irradiation dose according to the first embodiment.

In the control portion 80, the main dosimeter counter 81 counts the number of pulses output from the main dosimeter 50a, and as in the conventional technique, outputs the spot switch command when the count value a1 reaches the preset count A1.

Meanwhile, the abnormality determination portion 90 performs second abnormality determination (part 1) using the count value a3 of the second main dosimeter counter 95 and the count value b3 of the second sub dosimeter counter 94, in addition to the first abnormality determination using the count value b1 of the sub dosimeter counter 91 and the count value a2 of the main dosimeter (for leakage dose) counter 92 as in the conventional technique.

As described, in the first abnormality determination, the count value b1 of the sub dosimeter counter 91 is compared with the value of the sub dosimeter preset count B1 just before the switch of the spot. It is determined that there is an abnormality if the count value b1 exceeds the preset count B1 or if the ratio between the count value b1 and the preset count B1 is below a certain ratio. It is also determined that there is an abnormality if the count value a2 of the main dosimeter counter (for leakage dose) 92 exceeds the preset count A2 during the termination of the beam emission.

Meanwhile, in the second abnormality determination (part 1), the count value a3 of the second main dosimeter counter 95 that counts the number of pulses of the main dosimeter 50a is compared with the preset count value A3 for second abnormality determination defined by a pattern file 90a, independently from the first abnormality determination. It is determined that there is an abnormality if the count value a3 is out of a predetermined reference range based on the preset count value A3. Similarly, the count value b3 of the second sub dosimeter counter 94 that counts the number of pulses of the sub dosimeter 50b is compared with the preset count value B3 for second abnormality determination (B3 and A3 are usually set to a same value) defined in the pattern file 90a. It is also determined that there is an abnormality if the count value b3 is out of a predetermined reference range based on the preset count value B3.

As a result of adding the second abnormality determination (part 1), the abnormality can be detected even if both the main dosimeter 50a and the sub dosimeter 50b are in an abnormal state, such as when the high voltage power supplies of the main dosimeter 50a and the sub dosimeter 50b are not in a voltage output state. The excessive irradiation does not occur, and a safe particle beam irradiation apparatus can be provided.

The determination period of the second abnormality determination (part 1) is usually a period shorter than the determination period of the first abnormality determination. In the first abnormality determination, the determination is based on a period of changing the beam spot position (for example, period of 100 μm to 100 ms, although the period varies depending on the treatment planning and the like). Meanwhile, the determination period of the second abnormality determination is a period significantly shorter than an average changing period of the beam spot, e.g. a certain period shorter than 1/10 of the average changing period of the beam spot (for example, 100 μs to 1 ms). Therefore, the second main/sub dosimeter counters 95 and 94 are reset in each determination period. The short determination period allows outputting the interlock signal in a short time to terminate the beam emission without waiting for update timing of the beam spot when there is an abnormality in the irradiation dose. The possibility of the excessive irradiation can be further reduced.

(4) Second Embodiment

Second Abnormality Determination (Part 2)

Abnormality determination according to a second embodiment is performed in parallel with the abnormality determination in the first embodiment (the first abnormality determination and the second abnormality determination (part 1)). Specifically, it is determined that there is an abnormality when an absolute value of a difference between the count value a3 of the second main dosimeter counter 95 and the count value b3 of the second sub dosimeter counter 94 exceeds a predetermined threshold. The main dosimeter 50a and the sub dosimeter 50b usually have the same configuration. Therefore, if the main dosimeter 50a and the sub dosimeter 50b are both normal, the same number of pulses would be measured. Consequently, it is determined that there is an abnormality in one of the main/sub dosimeters 50a and 50b or one of the second main/sub dosimeter counters 95 and 94 if the absolute value of the difference between the count value a3 and the count value b3 exceeds a predetermined threshold. The interlock signal is generated to terminate the beam emission. The second embodiment further improves the reliability of the abnormality determination.

Figure 12:
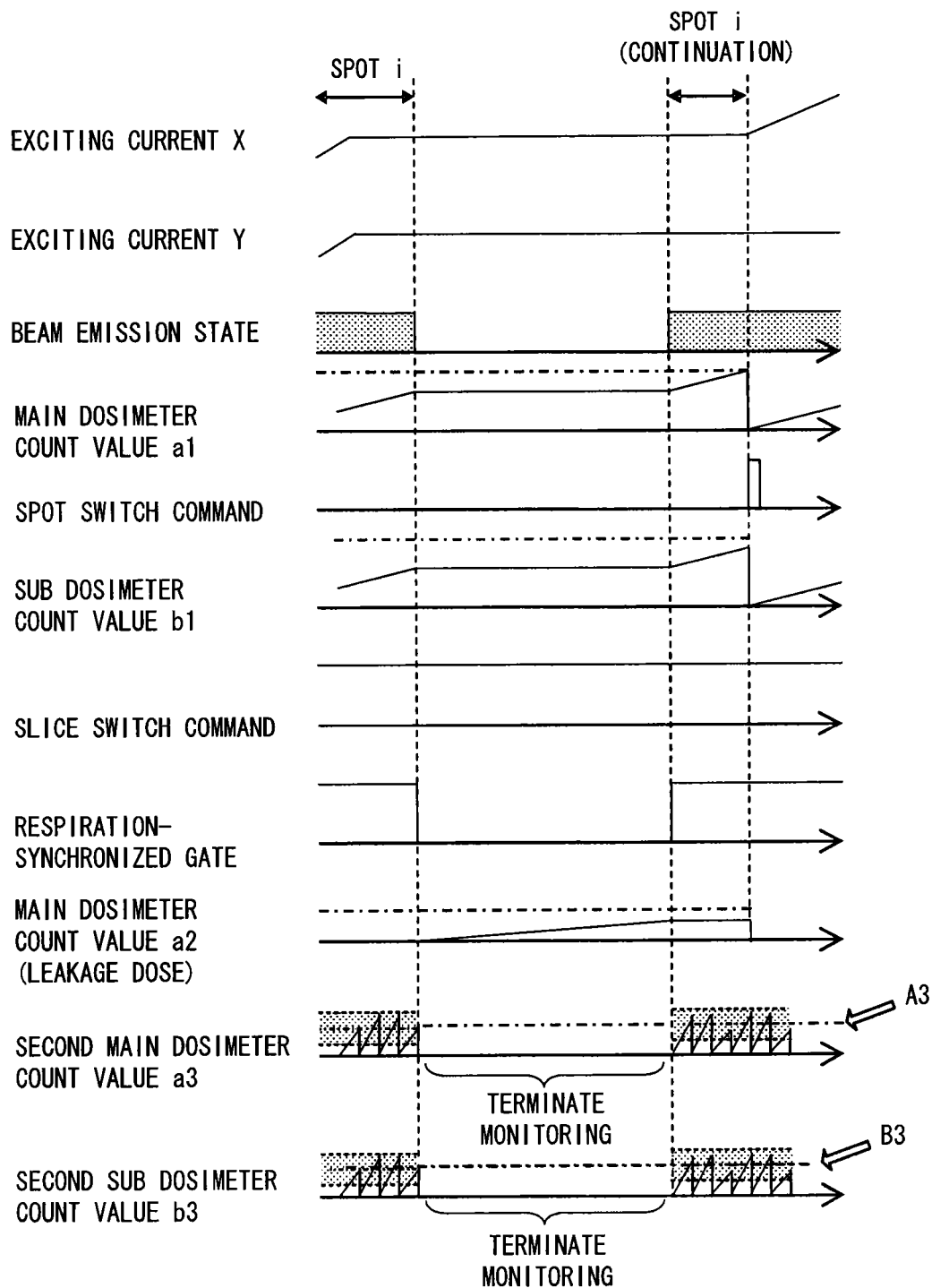
FIG. 12 is a timing chart showing a state of control and management of the irradiation dose according to a second embodiment.

FIG. 12 is a timing chart describing a state of control and management of the irradiation dose. As described, the emission of the beam is not terminated during the change in the current of the electromagnet power supply in the raster scanning irradiation. However, the emission of the beam is terminated during the slice switch or when the respiration-synchronized gate is turned off. If the abnormality monitoring is effective during the termination of the beam emission, the difference (absolute value) exceeds the threshold because the count values a3 and b3 are small. There is a high possibility of erroneous output of the interlock signal. Therefore, the abnormality determination is carried out only in the beam emission state. As a result, the reliability of the abnormality determination can be improved without generating an unnecessary interlock signal during the termination of the beam emission due to the slice switch or when the respiration-synchronized gate is turned off. Although FIG. 12 illustrates a determination condition when the beam is off due to the respiration-synchronized gate, the determination condition is similar when the beam is off due to the slice switch.

(5) Third Embodiment

Second Abnormality Determination (Part 3)

Figure 13:
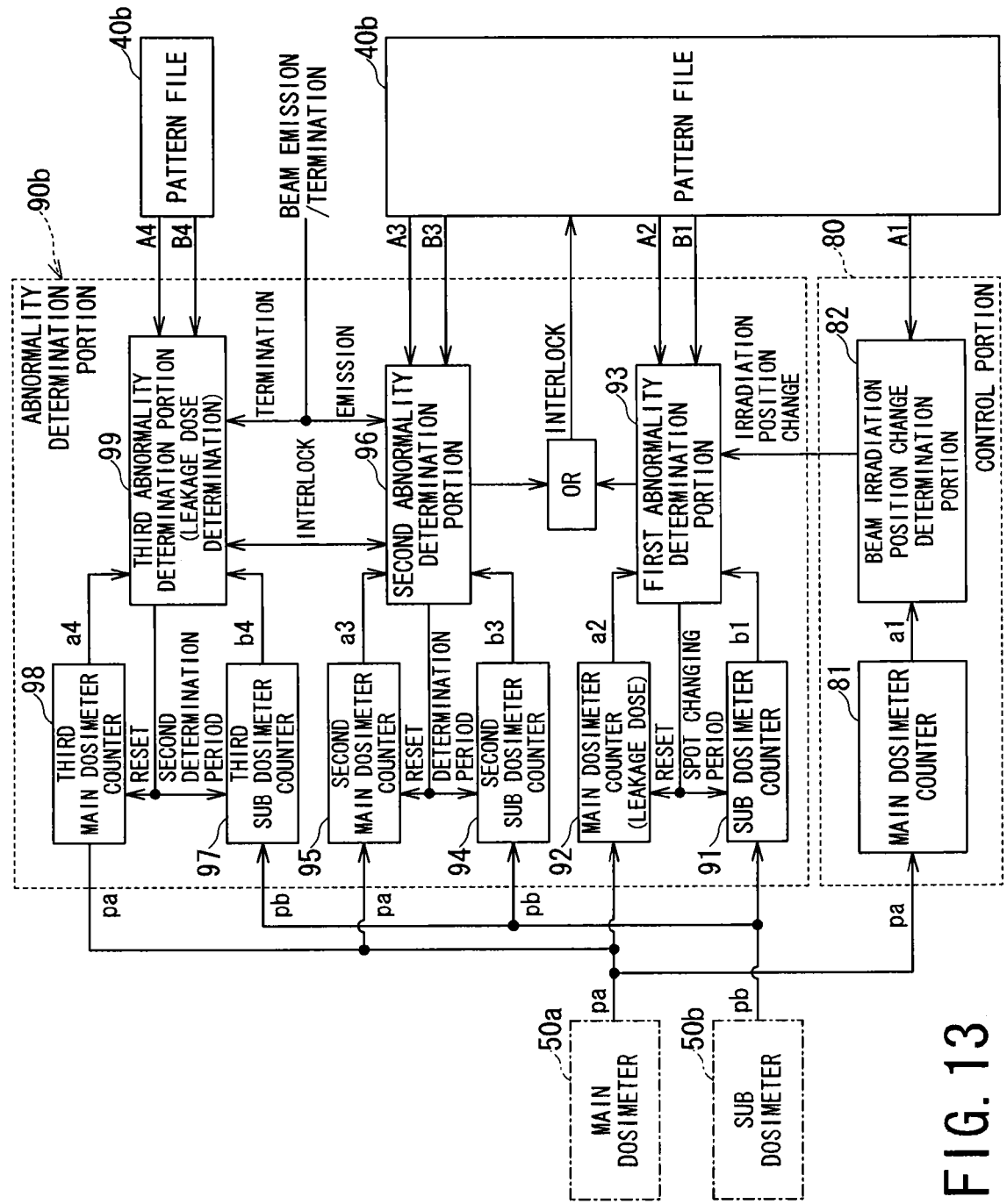
FIG. 13 is a diagram showing an example of configuration of an abnormality determination portion according to a third embodiment.

FIG. 13 is a diagram showing an example of configuration of an abnormality determination portion 90b according to a third embodiment. Third main/sub dosimeter counters 98 and 97 as well as a third abnormality determination portion 99 that performs leakage dose determination are added to the abnormality determination portion 90 of the first and second embodiments to form the abnormality determination portion 90b.

The third abnormality determination portion 99 compares count values a4 (third sectional dose measurement value) and b4 (fourth sectional dose measurement value) of pulses (pulses caused by leakage dose) output from the third main/sub dosimeter counters 98 and 97 during the termination of the beam emission with preset count values A4 (third reference value) and B4 (fourth reference value) for third abnormality determination defined in a pattern file 40b, respectively. If the count value exceeds the preset count value in at least one of the comparisons, the third abnormality determination portion 99 determines that there is an abnormality in the leakage dose (greater than expected leakage dose is generated) and outputs the interlock signal to the emission control portion 20. The above described abnormality determination for the leakage dose is second abnormality determination (part 3).

FIG. 14 is a diagram showing an example of the irradiation pattern file 40b used in the third embodiment, and the preset count values A4 and B4 for third abnormality determination are added to the right end. The preset count values A4 and B4 for third abnormality determination are thresholds for determining the leakage dose during the termination of the beam emission. Therefore, values smaller than the other preset count values are set.

Figure 15:
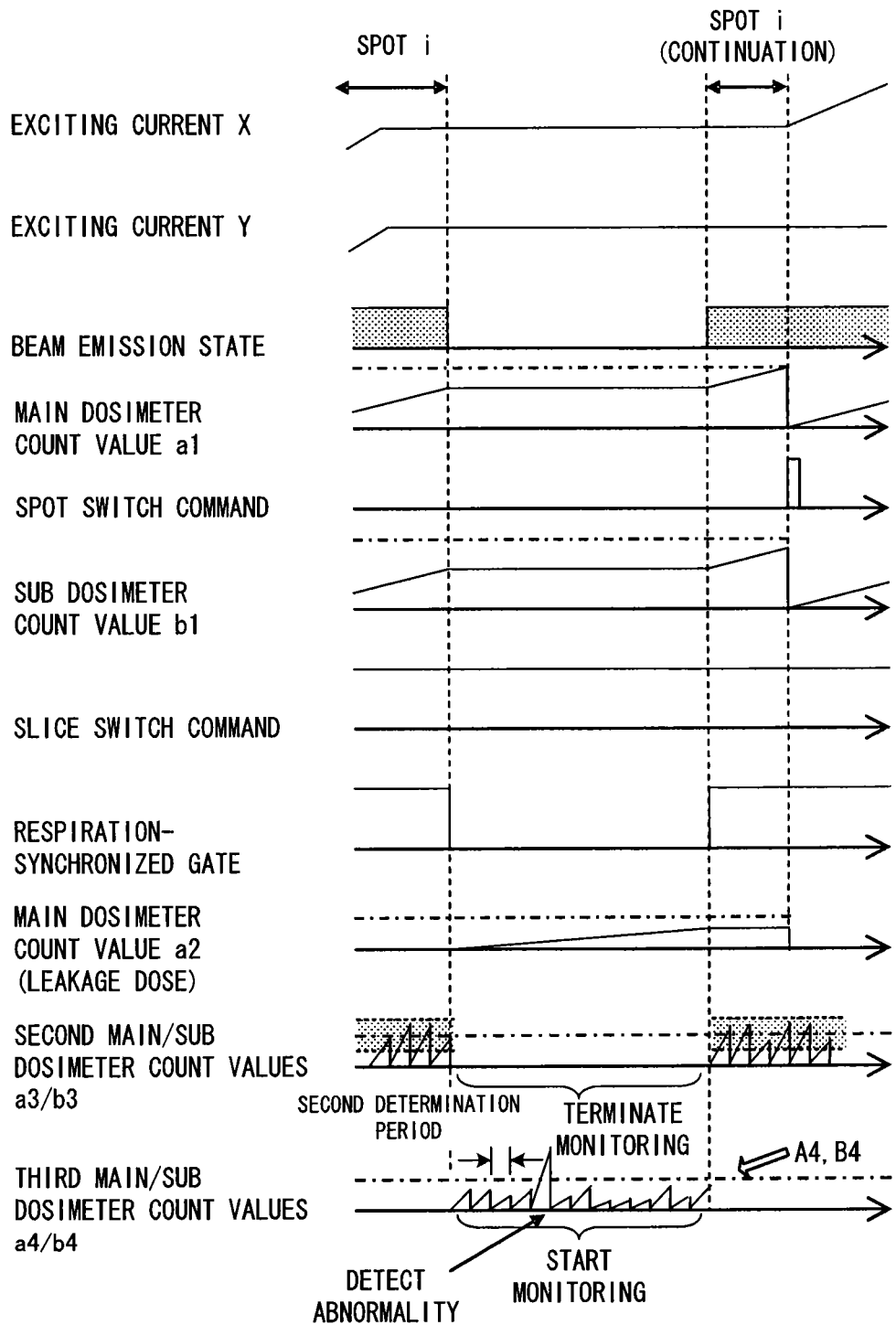
FIG. 15 is a timing chart showing a state of control and management of the irradiation dose according to the third embodiment.

FIG. 15 is a timing chart describing a state of control and management of the irradiation dose according to the third embodiment.

The third main/sub dosimeter counters 98 and 97 are characterized by integrating the number of pulses of the pulse signals from the main/sub dosimeters 50a and 50b at a sufficiently shorter interval (second determination period), such as about 100 μs to 1 ms, than the beam emission termination time. If the integrated count values a4 and b4 exceed the preset counts A4 and B4 set in the irradiation pattern file 40b, it is determined that greater than the defined leakage dose is generated, and the interlock signal is output to terminate the beam emission.

As shown in FIGS. 7, 8, and the like, in the conventional leakage dose determination, the number of pulses is continuously integrated without resetting during the termination period of the beam emission. Therefore, as described, the pulses caused by the internal noise of the main dosimeter 50a are constantly integrated during the termination period of the beam emission. The spike-like leakage dose is buried in the internal noise, and the detection sensitivity for momentary leakage dose cannot be sufficiently increased.

On the other hand, the third embodiment of the second abnormality determination (part 3), the integration period of the third main/sub dosimeter counters 98 and 97 (i.e. second determination period) is sufficiently shorter than the termination period of the beam emission. Therefore, the amount of integration of the number of pulses caused by the internal noise of the main/sub dosimeters 50a and 50b is significantly reduced, and highly-sensitive detection of the spike-like leakage dose is possible. As a result, highly sensitive monitoring of the leakage dose is possible not only for the accumulative beam emission, but also for the momentary beam emission, when the beam emission is terminated due to the range switch or the off-state of the respiration-synchronized gate. A safe particle beam irradiation apparatus 1 can be provided.

In the second abnormality determination (part 3), the third main/sub dosimeter counters 98 and 97 different from the second main/sub dosimeter counters 95 and 94 used in the second abnormality determination (part 1) (or the second abnormality determination (part 2)) are separately arranged. However, the second main/sub dosimeter counters 95 and 94 and the third main/sub dosimeter counters 98 and 97 may be integrated, and the second main/sub dosimeter counters 95 and 94 may be used for the second abnormality determination (part 3). In this case, the count values output from the second main/sub dosimeter counters 95 and 94 during the termination of the emission of the particle beam serve as the count values a4 and b4, respectively.

The second abnormality determination (part 3) and the second abnormality determination (part 1) may be independently combined with the first abnormality determination or both may be combined with the first abnormality determination at the same time.

As described, according to the particle beam irradiation apparatus and the control method of the particle beam irradiation apparatus according to the present embodiments, highly reliable measurement of a dose of each beam is possible, and highly sensitive measurement of a leakage dose caused by momentary beam emission is possible.

The present invention is not limited to the embodiments, and the present invention can be embodied by modifying the constituent elements in an execution phase without departing from the concept of the present invention. Various inventions can be formed based on appropriate combinations of a plurality of constituent elements disclosed in the embodiments. For example, some constituent elements among all constituent elements illustrated in the embodiments may be deleted. Constituent elements across different embodiments may also be appropriately combined.

REFERENCE SIGNS LIST 1 particle beam irradiation apparatus
10 beam generation portion
20 emission control portion
30 beam scanning portion
50a main dosimeter
50b sub dosimeter
80 control portion
90, 90a, 90b abnormality determination portions

The invention claimed is:

1. A particle beam irradiation apparatus that directs a particle beam to an affected area of a patient, the particle beam irradiation apparatus comprising:
  an emission control portion that controls emission and termination of the particle beam;
  a control portion that sequentially changes an irradiation position of the particle beam for the affected area;
  first and second dosimeters that measure dose rates of the particle beam directed to the affected area; and
  an abnormality determination portion that uses dose measurement values obtained by accumulating the dose rates output from the first and second dosimeters to perform abnormality determination of the apparatus and that outputs, to the emission control portion, an interlock signal for terminating the emission of the particle beam when determining that there is an abnormality, wherein the control portion accumulates the dose rate output from the first dosimeter for each of irradiation positions of the particle beam to calculate a first beam dose measurement value and changes the irradiation position of the particle beam when the first beam dose measurement value reaches a first planned dose value predetermined for each of the irradiation positions, and the abnormality determination portion performs:

first abnormality determination of accumulating the dose rate output from the second dosimeter for each of the irradiation positions of the particle beam to calculate a second beam dose measurement value and determining that there is the abnormality if the second beam dose measurement value exceeds a second planned dose value that is set to a value higher than the first planned dose value when the first beam dose measurement value reaches the first planned dose value; and second abnormality determination of accumulating the dose rates output from the first and second dosimeters for each of predetermined determination periods to calculate sectional dose measurement values and determining that there is the abnormality based on the sectional dose measurement values.

2. The particle beam irradiation apparatus according to claim 1, wherein in the second abnormality determination, the dose rates output from the first and second dosimeters during an emission period of the particle beam are accumulated for each of the predetermined determination periods to calculate first and second sectional dose measurement values, and it is determined that there is the abnormality in at least one of a case in which the first sectional dose measurement value is out of a predetermined first reference range and a case in which the second sectional dose measurement value is out of a predetermined second reference range.

3. The particle beam irradiation apparatus according to claim 2, wherein in the second abnormality determination, it is further determined that there is the abnormality when an absolute value of a difference between the first sectional dose measurement value and the second sectional dose measurement value is out of a predetermined determination range.

4. The particle beam irradiation apparatus according to claim 2 or 3, wherein the predetermined determination periods are set shorter than an average change interval of the particle beam irradiation position.

5. The particle beam irradiation apparatus according to claim 1, wherein in the second abnormality determination the dose rates output from the first and second dosimeters in an emission termination period of the particle beam are accumulated for each of the predetermined determination periods to calculate third and fourth sectional dose measurement values, and it is determined that there is the abnormality in at least one of a case in which the third sectional dose measurement value exceeds a predetermined third reference value and a case in which the fourth sectional dose measurement value exceeds a predetermined fourth reference value.

6. The particle beam apparatus according to claim 5, wherein the predetermined determination periods are set shorter than the emission termination period of the particle beam.

7. A control method of a particle beam irradiation apparatus that directs a particle beam to an affected area of a patient, the control method comprising the steps of:

controlling emission and termination of the particle beam;

sequentially changing an irradiation position of the particle beam for the affected area;

measuring, by first and second dosimeters, dose rates of the particle beam directed to the affected area;

performing abnormality determination of the apparatus using dose measurement values obtained by accumulating the dose rates output from the first and second dosimeters; and terminating the emission of the particle beam using an interlock signal when determining that there is an abnormality, wherein in the step of changing the irradiation position of the particle beam, the dose rate output from the first dosimeter is accumulated for each of irradiation positions of the particle beam to calculate a first beam dose measurement value, and the irradiation position of the particle beam is changed when the first beam dose measurement value reaches a first planned dose value predetermined for each of the irradiation positions, and the step of performing the abnormality determination includes:

performing first abnormality determination of accumulating the dose rate output from the second dosimeter for each of the irradiation positions of the particle beam to calculate a second beam dose measurement value and determining that there is the abnormality if the second beam dose measurement value exceeds a second planned dose value that is set to a value higher than the first planned dose value when the first beam dose measurement value reaches the first planned dose value; and performing second abnormality determination of accumulating the dose rates output from the first and second dosimeters for each of predetermined determination periods to calculate sectional dose measurement values and determining that there is the abnormality based on the sectional dose measurement values.

8. The control method of the particle beam irradiation apparatus according to claim 7, wherein in the second abnormality determination, the dose rates output from the first and second dosimeters during an emission period of the particle beam are accumulated for each of the predetermined determination periods to calculate first and second sectional dose measurement values, and it is determined that there is the abnormality in at least one of a case in which the first sectional dose measurement value is out of a predetermined first reference range and a case in which the second sectional dose measurement value is out of a predetermined second reference range.

9. The control method of the particle beam irradiation apparatus according to claim 8, wherein in the second abnormality determination, it is further determined that there is the abnormality when an absolute value of a difference between the first sectional dose measurement value and the second sectional dose measurement value is out of a predetermined determination range.

10. The control method of the particle beam irradiation apparatus according to claim 8 or 9, wherein
   the predetermined determination periods are set shorter than an average change interval of the particle beam irradiation position.

11. The control method of the particle beam irradiation apparatus according to claim 7, wherein
   in the second abnormality determination
   the dose rates output from the first and second dosimeters in an emission termination period of the particle beam are accumulated for each of the predetermined determination periods to calculate third and fourth sectional dose measurement values, and it is determined that there is the abnormality in at least one of a case in which the third sectional dose measurement value exceeds a predetermined third reference value and a case in which the fourth sectional dose measurement value exceeds a predetermined fourth reference value.

12. The control method of the particle beam apparatus according to claim 11, wherein
   the predetermined determination periods are set shorter than the emission termination period of the particle beam.

\* \* \* \* \*